United States Patent [19]

Vanderpool

[11] Patent Number: 4,524,143

[45] Date of Patent: Jun. 18, 1985

[54] CATALYST FOR PREPARATION OF LINEAR POLYETHYLENEPOLYAMINES

[75] Inventor: Steven H. Vanderpool, New Braunfels, Tex.

[73] Assignee: Texaco Inc., White Plains, N.Y.

[21] Appl. No.: 455,154

[22] Filed: Jan. 3, 1983

[51] Int. Cl.$^3$ .............................................. B01J 27/14
[52] U.S. Cl. .................... 502/208; 502/214
[58] Field of Search ................................ 502/208, 214

[56] References Cited

U.S. PATENT DOCUMENTS

| | | | |
|---|---|---|---|
| 2,650,201 | 8/1953 | Mority | 502/214 |
| 2,656,323 | 10/1953 | Bielowski et al. | 502/214 |
| 2,811,416 | 10/1957 | Russell et al. | 502/214 |
| 3,044,954 | 7/1962 | Herschler | 502/214 X |
| 3,088,908 | 5/1963 | Hansford | 502/214 |
| 3,297,701 | 1/1967 | Brader et al. | 260/268 |
| 3,342,820 | 9/1967 | Brader | 260/268 |
| 3,634,286 | 1/1972 | Yates | 502/214 X |
| 3,962,134 | 6/1976 | Cobb | 502/214 X |
| 3,989,706 | 11/1976 | Ichikawa et al. | 502/214 X |
| 4,036,881 | 7/1977 | Brennan et al. | 260/583 |
| 4,044,053 | 8/1977 | Brennan et al. | 260/583 |
| 4,103,087 | 7/1978 | Brennan | 544/78 |
| 4,118,588 | 10/1978 | Fouquet et al. | 502/214 X |
| 4,314,083 | 2/1982 | Ford et al. | 564/479 |
| 4,316,840 | 2/1982 | Ford et al. | 260/239 |

FOREIGN PATENT DOCUMENTS

| | | | |
|---|---|---|---|
| 53-33989 | 3/1978 | Japan | 502/214 |
| 2092467 | 1/1982 | United Kingdom . | |

OTHER PUBLICATIONS

Refractories, Norton, 3rd Ed., 1949, p. 318, McGraw-Hill Book Co. Inc., New York, Toronto, London.

A. Winkler & E. Thilo (Deutsche Akad. Wiss. Berlin, Germany) Z. Anurg Chem, 346(1-2) 65 C.A. 14807c, 1966.

*Primary Examiner*—William G. Wright
*Attorney, Agent, or Firm*—Jack H. Park; R. A. Kulason; Kenneth R. Preim

[57] ABSTRACT

This invention is directed to thermally activated pelletted catalyst compositions comprising zirconium silicate having phosphorous deposited thereon and their use in the production of predominantly linear polyethylenepolyamines from ethylenediamine and monoethanolamine.

9 Claims, No Drawings

CATALYST FOR PREPARATION OF LINEAR POLYETHYLENEPOLYAMINES

BACKGROUND OF THE INVENTION

1. Technical Field of the Invention

This invention relates to the preparation of predominately linear polyethylenepolyamines from the starting reagents of ethylenediamine and monoethanolamine in the presence of unique catalyst compositions comprising zirconium silicate having a compound of phosphorous deposited thereon.

2. Prior Art

Heretofore, polyethylenepolyamine compounds such as diethylenetriamine, triethylenetetramine and the higher homologs have been produced by the reaction of an alkyl halide such as ethylene dichloride with an amine such as ammonia or ethylenediamine at elevated temperatures and pressures. Normally, relatively high yields of predominatly non-cyclic polyethylenepolyamine compounds are obtained from this process with varying yields of heterocyclic amines. The large amounts of energy required to produce the reactants as well as the difficult separation procedures required to recover the more valuable linear polyethylenepolyamines diminish the usefulness of the ethylene dichloride process. The hydrohalide salts of ammonia and the polyethylenepolyamine products must also undergo difficult and time consuming caustic neutralization to yield the free polyethylenepolyamines.

It has heretofore been known that phosphates can be used to catalyze reaction products to produce predominately heterocyclic rather than linear products. Thus, U.S. Pat. No. 3,297,701 teaches the use of aluminum phosphate to catalyse the reaction of ethanolamines and polyethylenepolyamines to yield cyclic compounds. U.S. Pat. No. 3,342,820 discloses the use of aluminum phosphate for the preparation of heterocyclic compounds such as triethylenediamine. As another example, U.S. Pat. No. 4,103,087 also discloses the use of aluminum phosphate catalysts for producing heterocyclic product compounds.

More recently, investigators have found that more linear products can also be obtained in a catalytic conversion. Thus, Ford et. al. U.S. Pat. No. 4,316,840 discloses the preparation of polyalkylenepolyamines from ethylene diamine utilizing a metal nitrate or sulfate as a catalyst. U.S. Pat. No. 4,314,083 discloses the reaction of ethylene diamine with monoethanolamine to prepare noncyclic polyalkylenepolyamines using, as a catalyst, a salt of a nitrogen or sulfur-containing compound.

In more recent inventions made in our laboratories, Brennan et. al. in U.S. Pat. No. 4,036,881 discloses the use of phosphorous-containing catalysts to catalyze the reaction of ethylenediamine with monoethanolamine. Excellent results were obtained when the reaction was conducted in an autoclave. However, when the phosphorous compound was supported on silica or diatomaceos earth, good results were obtained only at comparatively low conversions. Brennan et. al. U.S. Pat. No. 4,044,053 is also relevant in this regard. A recently filed Brennan copending application Ser. No. 283,713, filed July 16, 1981 (now abandoned) and entitled "Preparation of Linear Polyethylenepolyamines With an Aluminum Phosphate Catalyst" is directed to an aluminum phosphate catalyst. Excellent results were obtained using a catalyst of this nature in batch-type reactions. Brennan U.S. Pat. No. 4,103,087 discloses the use of pelleted aluminum phosphate to prepare di-(N,N-disubstituted amino)alkanes.

French Pat. No. 1,317,359 dated Feb. 8, 1963, discloses the preparation of granulated zirconium phosphate and its use as an ion-exchange resin. Winkler et al. in a 1966 publication [Deutsche Akad. Wiss., Berlin, Germany, Z. Anorg. Allgen. Chem. 346 (1-2), 92–112 (1966)] disclose compounds of the general formula $HX^vP_2O_3$ wherein X represents arsenic, antimony and mixtures thereof. Also disclosed are compounds of the general formula $H_2X^{iv}P_2O_3$, wherein X represents silicon, germanium, tin, lead, titanium and zirconium. It is shown that the group IV phosphates ., have cation exchange properties.

Daniel Br. Apcn. No. 2,092,467 pub. Aug. 18, 1982, modifies iron phosphate catalysts disclosed in Cavaterra U.S. Pat. No. 3,948,959 for making methacrylic acid from isobutyric acid. Daniel uses such catalysts in admixture with a support prepared by calcining the dried powder recovered from a slurry of silica with phosphoric acid. Daniel teaches that the support is inert and that titania or zirconia can also be used.

SUMMARY OF THE INVENTION

A method of preparing a novel phosphorous-containing catalyst is disclosed. The catalyst is extremely useful in the improved production of predominatly linear polyethylenepolyamines from ethylenediamine and monoethanolamine reactants. The novel catalysts of the claimed invention can be prepared by treating zirconium silicate with a phosphorous compound such that, in a thermally activated condition, the phosphorous is chemically bound to the zirconium silicate. These novel compositions can be used to catalyze the reaction of monoethanolamine with ethylenediamine to provide essentially linear polyethylenepolyamine reaction products.

DETAILED DESCRIPTION

In one aspect the invention is directed to an improved catalyst composition comprising zirconium silicate to which phosphorous has been bonded by thermal activation. In another aspect of the present invention, such catalysts are used in producing essentially linear polyethylenepolyamines such as diethylenetriamine, triethylenetetramine, tetraethylenepentamine and pentaethylenehexamine from the reaction of ethylenediamine and monoethanolamine. The inventor is unaware of the precise structural differences between the claimed catalysts and previous phosphate catalysts which have been tried in such reactions, but is cognizant of substantially higher rates of conversion to linear polyethylenepolyamines with the claimed catalysts.

The novel compositions of the present invention catalyze the reaction of ethylenediamine and monoethanolamine at a temperature of from about 250° C. to about 400° C., preferably from about 300° C. to about 350° C. and a pressure of from about 500 to about 3000 psig. and preferably from about 1000 to about 3000 psig., more preferably from about 1000 to 2000 psig. The ratio of ethylenediamine to monoethanolamine may range from about 1:2 to about 5:1. Higher temperatures or higher pressures may be used, but there is no particular advantage in using higher temperatures and/or pressures.

The pelleted catalyst compositions of the present invention are normally employed as a fixed bed of catalyst in a continuous reaction system. In a continuous process of this nature, the time of contact of the reactants with the catalyst is one of the interrelated factors that those skilled in the art will adjust, along with temperature, pressure, bed geometry, pellet size, etc. in order to obtain a desired rate of reaction and, hence, a desired percentage of conversion of the reactants. Thus, in a continuous process, it is not necessary to drive the reaction to completion because unreacted feedstock components can be recycled to the reactor.

It is customary to use cylindrically-shaped catalyst pellets having a diameter essentially equal to the length thereof, such as diameters and lengths ranging from about 1/32" to about ⅜". It will be understood that the shape and dimensions of the pellets are not critical to the present invention and that pellets of any suitable shape and dimensions may be used as desired, by one wishing to practice the process of the present invention.

When cylindrical pellets of catalyst of the type described above are used, the wiehgted hourly space velocity may be varied within wide limits (e.g., 0.1 to 5 w/hr/w) in order to obtain a desired rate of conversion, as explained above. Normally, space velocities of about 0.5 to 2 w/hr/w will be employed.

Catalyst life is an important factor in conducting a continuous reaction. For example, if a catalyst is easily poisoned, or if catalyst pellets do not have good structural properties, the economics of the process will be seriously and adversdly affected.

The catalysts of the present invention are not particularly susceptible to poisoning so this normally does not present a problem. However, under the reaction conditions employed, amines of the type used and formed herein have the potential capability of leaching or otherwise adversely affecting the structural integrity of the pellets. In an extreme instance, catalyst pellets having good initial crush strength and surface hardness will be reduced to fines very rapidly when used under reaction conditions such as those employed herein.

It is a feature of the present invention that the pelleted catalyst compositions have improved resistance to physical degradation when used to catalyse the reaction of monoethanolamine with ethylenediamine.

The catalyst compositions of the present invention are prepared by depositing a phosphorus compound on a support comprising zirconium silicate.

Any appropriate liquid or liquifiable phosphorus compound can be used as a source of the phosphorus. For convenience, phosphoric acid will normally be used. However, other phosphorus compounds such as phosphoryl chloride ($POCl_3$), phosphorous acid, polyphosphoric acid, phosphorus halides, such as phosphoryl chloride or phosphorus bromide, alkyl phosphates and alkyl phosphites such as trimethyl phosphate, triethyl phosphate, trimethyl phosphite, triethyl phosphite, etc. may be utilized. In general, the pelleted composition should contain at least about 0.5 weight percent of phosphorus.

When the catalyst composition is to be prepared by impregnating a preformed pellet, a suitable procedure to be used is to heat a liquid containing the liquid or liquifiable phosphorus compound at a temperature of about 100° to about 150° C. and to then add pellets in an amount about equal to the volume of the heated liquid. This treatment should be continued from about 0.5 to about 5 hours. At the end of that time, the resulting slurry may be cooled, decanted to remove excess liquid followed by washing with an amount of water adequate to substantially completely remove un-adsorbed liquid. Temperatures above 150° C. can be doing so.

It will be understood that the phosphorous that is present on a thus-treated pellet is not present as elemental phosphorous, but rather as phosphorous that is chemically bound, probably as an oxide, to the support. This is, demonstrated by the fact that repeated washing will not remove all of the phosphorous. However, the exact nature of the bonding is not completely understood.

The amount of phosphorous that is bonded or otherwise adheres to the support is a function of heating and other conditions used in the treating step and is also a function of the chemical identity of the phosphorous compound that is used as a source of phosphorous. Under the treating conditions exemplified above, at least about 2.5 wt. % of phosphorous is caused to bond or otherwise permanently adhere to the pellets. There is an upper limit to the amount of phosphorous that bonds or otherwise permanently adheres to the support. This upper limit is, as indicated, a function of both the treating conditions and the chemical used as a source of the phosphorous. Normally, the maximum amount of phosphorous that can be caused to bond or otherwise permanently adhere to the pellets is within the range of about 5 to 10 wt. %.

As a matter of convenience, the normal practice is to use only one chemical as a phosphorous source (e.g., phosphoric acid). However, mixtures of two or more such reagents may be used, if desired.

When the pellets are impregnated with the phosphorous compound at a temperature of at least about 100° C., there is no absolute need to calcine the catalyst composition before use. However, the pellets can be calcined, if desired, as a precautionary measure and/or in order to still further improve the physical properties of the pellets. The pellets are suitably calcined at a temperature of about 200° C. to about 800° C. for a period of time within the range of 2 to 24 hours; more preferably at a temperature of about 500° C. to about 700° C. for about 4 to 16 hours.

Other procedures can be used in adding phosphorous to the support. For example, the pellets can be treated with the phosphorous compound at ambient temperatures or at more modest elevated temperatures of less than about 100° C. In this situation, however, it is necessary to thermally activate the treated pellets by calcining under the conditions recited above.

Alternatively, the support can be treated with the phosphorous-containing compound in powdered form and the powder can thereafter be pelleted. If the treatment is conducted at a temperature of about 100° C. or more, thermal activation will normally have been obtained and it will not be absolutely necessary to perform a calcining operation. If lower treating temperatures are used, calcining is a desired operation. The calcining operation can be conducted prior to or subsequent to the pelleting step. Any appropriate pelleting procedure of the type known to those skilled in the art may be used. For example, the treated powdered support can be mixed with graphite and/or other binders and compacted or extruded under conventional conditions.

There are many compounds which can be formed from the reaction of ethylenediamine and monoethanolamine besides the preferred linear polyethylenepolyamines such as diethylenetriamine, triethylenetetramine, tetraethylenepentamine and pentaethylenehexamine. Less desirable cyclics and other compounds, such as piperazine, N-(2-aminoethyl)ethanolamine and N-(2-aminoethyl)piperazine, are also formed. The more desired linear polyethylenepolyamines can be easily recovered from the reaction product mixture by conventional methods such as distillation. Such distillation recovery methods are well known in the art. An outstanding advantage of the claimed invention is that the lower molecular weight polyethylenepolyamines recovered from the reaction mixture can be further reacted with monoethanolamine to produce a larger percentage of the higher molecular weight linear polyethylenepolyamines.

The following examples will further illustrate the preparation of predominantly linear polyethylenepolyamines from ethylenediamine and monoethanolamine by the use of the catalyst compositions of the present invention. They are given by way of illustration and not as limitations on the scope of the invention. Thus, it will be understood that reactants, proportions of reactants, and time, temperature and pressure of the reaction steps may be varied with much the same results achieved.

For purposes of convenience and brevity, the reactant compounds employed and the products obtained have been abbreviated in the following examples and tables. The abbreviations employed for these various compounds are:

EDA—ethylenediamine
MEA—monoethanolamine
PIP—piperazine
DETA—diethylenetriamine
TETA—triethylenetetramine
TEPA—tetraethylenepentamine
AEEA—N-(2-aminoethyl)ethanolamine
AEP—N-(2-aminoethyl)piperazine
HEP—N-(hydroxyethyl)piperazine.

EXAMPLE I

Catalyst Preparation

Zirconium silicate commercially available from Alfa Products, Ventran Division of Danvers, Mass., was pelletted. The pellets were heated at 130° C. for 5 hours in 85% $H_3PO_4$, washed, dried and calcined at 600° C. for 16 hours.

EXAMPLE II

Reaction of Monoethanolamine with Ethylenediamine

A reactor suitable for continuous operations was filled with pellets of Example I. A mixture of ethylenediamine and monoethanolamine in the weight ratio of 2:1 was continuously charged to the reactor at a feed rate of one LHVS and a reactor back-pressure of 1500 psig. The temperature was adjusted at 304° C. to give a 65 wt. % conversion of the MEA.

EXAMPLE III

Comparative Runs

Example II was repeated, except that the pelletted catalyst that was used was a 40 wt. % phosphate on alumina catalyst as disclosed in Brennan U.S. Pat. No. 4,103,087 at column 8, lines 50-54. Reaction conditions were the same, except that it was necessary to adjust the temperature to 329° C. in order to obtain a 65 wt. % conversion of the MEA.

The results of the tests are set forth below. The data is based on analysis of the crude reaction effluent calculated on a feed-free basis.

TABLE 1

| Example | II | III |
|---|---|---|
| Temp., 65% MEA Conv. | 304 | 329 |
| PIP, wt % | 4.6 | 5.2 |
| DETA, wt % | 62.4 | 38.5 |
| AEEA, wt % | 0.3 | 2.6 |
| AEP & HEP, wt % | 3.4 | 4.5 |
| TETA, wt % | 16.1 | 18.3 |
| TEPA, wt % | 2.2 | 5.9 |
| % non-cyclics in TETA | 92 | 77 |

As can be seen from Table I, the catalyst of the present invention was significantly more active than the reference catalyst. Selectively to DETA was outstanding. Also, there was a significant decline in the yield of undesirable cyclic products such as piperazine, aminoethylpiperazine and hydroxyethylpiperazine.

There are times when it is desirable to obtain a greater yield of TETA and/or TEPA than the yield demonstrated herein. In such instances, the DETA can be recycled by substituting DETA for all or a part of the ethylenediamine feedstock.

The foregoing examples have been given by way of illustration only and are not intended as limitations on the scope of the present invention, which is defined by the following claims.

I claim:

1. As a new composition of matter, a thermally activated pelleted composition consisting essentially of zirconium silicate having from about 0.5 wt. % to about 10 wt. % of phosphorous thermally chemically bonded thereto.

2. A composition as in claim 1, wherein the source of the phosphorous is phosphoric acid.

3. A method of preparing a catalyst composition which comprises impregnating pellets of zirconium silicate with a liquid phosphorous compound and heating the impregnated pellets at a temperature of about 100° to about 150° C. for a period of time ranging from about 0.5 to about 5 hours sufficient to thermally chemically bond 0.5 wt. % to about 10 wt. % of phosphorous to the zirconium silicate, thereafter recovering the thus treated pellets, next water washing the thus-treated pellets to remove chemically uncombined phosphorous and then drying the pellets.

4. A method as in claim 3, wherein the source of phosphorous is phosphoric acid.

5. As a new composition of matter, a thermally activated pelleted composition consisting essentially of zirconium silicate having from about 0.5 wt. % to about 10 wt. % of phosphorous thermally chemically bonded thereto, said catalyst composition having been prepared by:

impregnating pellets of zirconium silicate with a liquid phosphorous compound and heating the impregnated pellets at a temperature of about 100° to about 150° C. for a period of time ranging from about 0.5 to about 5 hours sufficient to thermally chemically bond 0.5 wt. % to about 10 wt. % of phosphorous to the zirconium silicate, thereafter recovering the thus-treated pellets, next water washing the thus-treated pellets to remove chemically uncombined phosphorous and then drying the pellets.

6. A composition as in claim 5, wherein the said dried pellets are also calcined at a temperature of about 200° to about 800° C. for a period of time within the range of about 2 to 24 hours.

7. A composition as in claim 6, wherein the source of the phosphorous is phosphoric acid.

8. A method of preparing a catalyst composition which comprises impregnating pellets of zirconium silicate with a liquid phosphorous compound and heating the impregnated pellets at a temperature of about 100° to about 150° C. for a period of time ranging from about 0.5 to about 5 hours sufficient to thermally chemically bond 0.5 wt. % to about 10 wt. % of phosphorous to the zirconium silicate, recovering the thus-treated pellets, water washing the thus-treated pellets to remove chemically uncombined phosphorous, drying the pellets, and then calcining said dried pellets at a temperature of about 200° to about 800° C. for a period of time within the range of 2 to 24 hours.

9. A method as in claim 8, wherein the source of the phosphorous is phosphoric acid.

* * * * *